United States Patent [19]

O'Keeffe

[11] Patent Number: 4,936,858
[45] Date of Patent: Jun. 26, 1990

[54] IMPLANTABLE FABRIC POUCH FOR MAMMARY PROSTHESIS

[76] Inventor: Paul O'Keeffe, 1 Barana Parade, Roseville Chase, New South Wales, 2069, Australia

[21] Appl. No.: 198,728

[22] Filed: May 24, 1988

Related U.S. Application Data

[63] Continuation of Ser. No. 891,210, Jul. 28, 1986, abandoned, which is a continuation-in-part of Ser. No. 861,082, May 8, 1986, abandoned.

[51] Int. Cl.⁵ ............................................. A61F 2/12
[52] U.S. Cl. ....................................... 623/8; 600/37
[58] Field of Search ................ 600/37; 623/7, 8, 12, 623/1; 128/334 R

[56] References Cited

U.S. PATENT DOCUMENTS

| | | | |
|---|---|---|---|
| 3,878,568 | 4/1975 | Connolly | 623/7 |
| 3,914,802 | 10/1975 | Reick | 623/1 |
| 4,205,401 | 6/1980 | Frisch | 623/8 |
| 4,347,847 | 9/1982 | Usher | 128/334 R |
| 4,403,604 | 9/1983 | Wilkinson et al. | 623/12 |
| 4,428,375 | 1/1984 | Ellman | 128/334 R |
| 4,441,215 | 4/1984 | Kaster | 623/1 |
| 4,469,101 | 9/1984 | Coleman | 128/334 R |
| 4,483,339 | 11/1984 | Gillis | 128/334 R |
| 4,587,969 | 5/1986 | Gillis | 128/334 R |

*Primary Examiner*—Richard J. Apley
*Assistant Examiner*—James Prizant
*Attorney, Agent, or Firm*—Bryan, Cave, McPheeters & McRoberts

[57] ABSTRACT

The present invention discloses a pouch to contain a mammary implant formed from a net-like material fabricated from a bio-compatible non-biodegradable yarn; the pouch being so constructed that the surface intended to form the anterior layer in use is relatively inextensible in the vertical direction as compared with at least one axis non-parallel thereto.

15 Claims, 2 Drawing Sheets

IMPLANTABLE FABRIC POUCH FOR MAMMARY PROSTHESIS

This is a continuation of U.S. application Ser. No. 891,210, filed 7/28/86, (abandoned), which is a continuation-in-part of application Ser. No. 861,082, filed May 8, 1986, (abandoned) and also entitled "Implantable Fabric Pouch For Mammary Implants".

The present invention relates to mammary prosthesis and in particular to an implantable fabric pouch for encapsulating such mammary prosthesis.

For a number of years surgeons have augmented and changed the shape of womens breasts by the introduction of mammary prosthesis into the breast area. Typically these mammary protheses have comprised a closed silicone sac filled with gel or saline solution.

Most patients experience satisfactory mammary augmentation immediately following the implantation procedure with the breasts simulating natural breasts in contour, appearance, feel and dynamics. However during a relatively short period after the implantation procedure, usually about six months, many patients experience a contracture of the tissue surrounding the mammary prosthesis causing it to assume a spherical shape and other unnatural attributes. In addition to the upper surface of the breast tending to display unnatural convexity the breast may also become tight and not freely moveable.

This problem with mammary protheses has been appreciated for some years and for example U.S. Pat. No. 3934274 seeks to overcome the problem by use of a double lumen prosthesis having an outer and an inner chamber, the outer chamber of which may be evacuated once tissue contracture is experienced thereby relieving the forces exerted by the tissue and alleviating the unnatural tendency of the prosthesis to adopt spherical shape.

To date however a satisfactory longterm solution to the problem of tissue contracture about a mammary implant has not been found and this may perhaps be due to the lack of understanding of the reasons for such tissue contracture.

It is an object of the present invention to reduce the incidence of tissue contracture around a mammary implant.

Accordingly the present invention discloses an implantable pouch to contain a mammary prosthesis formed from a net-like material fabricated from a biocompatible non-biodegradable yarn; the pouch being so constructed that the surface intended to form the anterior layer in use is relatively inextensible along the cephalic-caudal axis as compared with at least one axis non-parallel thereto.

The present invention additionally discloses a method of performing a mammary implant operation comprised of the steps of:

(a) Selecting a pouch in accordance with the present invention having a diameter of between 0 and 40 percent greater than the equilibrium diameter of the prosthesis which it is to contain;
(b) Placing the prosthesis within the pouch;
(c) Locating and pouch and prosthesis in the breast such that the anterior layer of the pouch is relatively inextensible along the cephalic-caudal axis.

One embodiment of the present invention will now be described with reference to the accompanying drawings in which.

Figure 1:
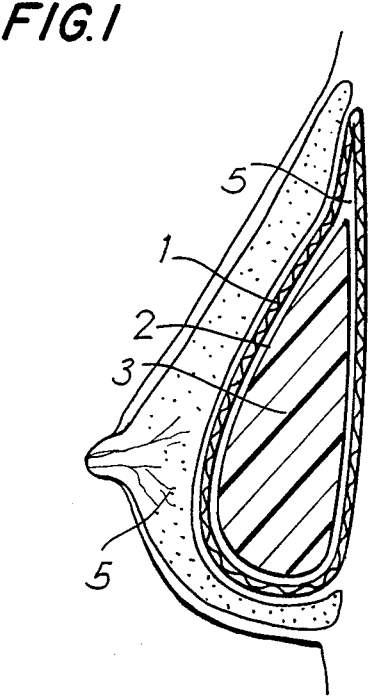
FIG. 1 is a side elevation of a breast with a mammary prothesis in a pouch in accordance with the present invention in vertical section.

FIG. 1 depicts a pouch 1 in accordance with the present invention encapsulating a silicone mammary prosthesis 2 filled with gel 3. Breast tissue 4 is shown around the anterior surface of the pouch. It will be noted that the mammary prosthesis is a loose fit inside the pouch in order that the prosthesis may adopt a natural teardrop shape there being excess space inside the pouch at 5.

Figure 2:
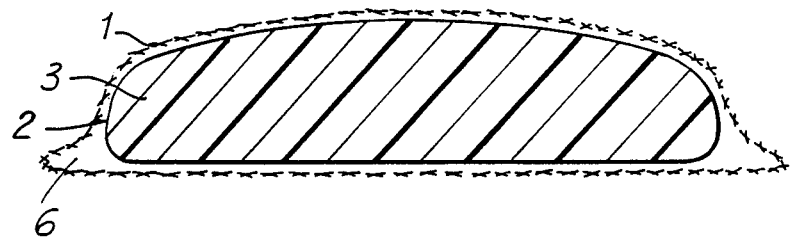
FIG. 2 is a side elevation in vertical section along the diameter of a mammary prosthesis and pouch in accordance with the present invention in an equilibrium position.

It has been found desirable that the pouch be slightly greater in diameter than the prosthesis and in the example depicted at FIG. 2 the pouch diameter exceeds the diameter of the prothesis in its equilibrium position by approximately 20 percent. If the prosthesis of FIG. 2 were 10 centimeters in diameter there would consequently be a clearance of approximately one centimeter at areas 6 and 7.

Figure 3:
FIG. 3 is a side elevation in vertical section along the diameter of a mammary prosthesis and pouch in accordance with the present invention in a flattened non-equilibrium state.

This excess space inside the pouch allows the silicone prosthesis to spread or expand or balloon to a limited extent when deformed as depicted in FIG. 3 until is occupies the entire lumen of the pouch. This ensures that the breast will not feel overly tight and will maintain soft and flexible to the touch.

Figure 4:
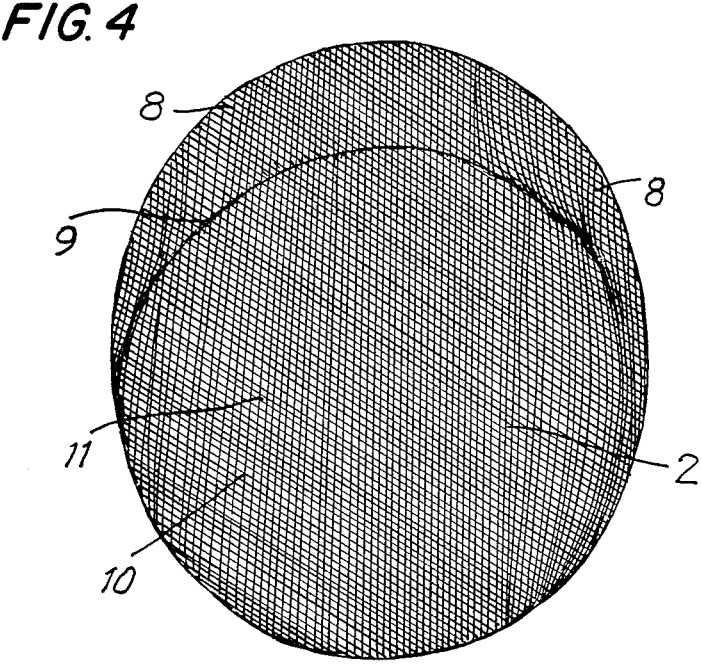
FIG. 4 is an anterior view of a mammary prosthesis inside a pouch in accordance with the present invention as it would appear with the patient standing.
Figure 5:
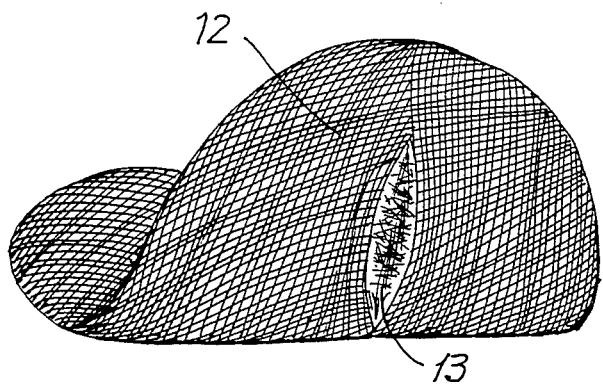
FIG. 5 is a perspective view of a pouch in accordance with the present invention which has been lifted to show part of the posterior layer.

FIGS. 4 and 5 depict the orientation of the yarns comprising the pouch with respect to the mammary prosthesis.

As may best be viewed from FIG. 4 the fabric of the pouch has strands 8 running along the cephalic-caudal axis and according to the present invention these strands are relatively inextensible. The mammary implant 2 may be seen within the pouch, the upper extremity of the prosthesis being the semi-circle 9. This view indicates the orientation of the prosthesis with respect to the pouch with the patient in a standing position. The prosthesis is naturally maintained in the lower part of the pouch under the influence of gravity.

The term inextensible where used throughout this specification refers to the extensibility of the fabric of a pouch along a certain axis but calculated after the pouch has been implanted in the body for a period of time adequate to achieve substantial ingrowth of body tissue through the fabric. It is necessary to define the extensibility of the fabric in this manner for the following reason.

The embodiments depicted herein with reference to FIGS. 4 and 5 depict inextensible yarn running parallel to the axes along which the fabric of the pouch is intended to be inextensible. Consequently the extensibility of the fabric in this example corresponds exactly to the extensibility of the yarn from which the fabric is manufactured. This relationship between the extensibility of the fabric and the yarn along these axes is of course the same both before and after the pouch is implanted in a patient.

Pouches have however been constructed from fabrics in which the yarn does not run parallel to the cephalic-caudal axis or other axes intended to carry stress but such pouches nevertheless achieve inextensibility along the said axes once implanted and invaded by body tissue. For example the fabric can be a tulle net which is supplied pre-stressed in one direction. This will produce a diamond pattern between the fabric yarns with the long axis of the diamonds aligned in the direction of stress. After implantation in the body and as the diamonds fill with tissue the fabric will stabilise and will be far less extensible along the axis corresponding to the long axes of the diamond pattern in the fabric than along the short axes of the diamonds. The fabric is pre-stressed in the sense that the cross over points for the fabric yarns are fixed such that diamond like pattern in the fabric is of a configuration which gives the desired resistance to distension along certain axes.

It has been found that if the pouch is relatively inextensible on the anterior side along the cephalic-caudal axis that contracture of the tissue surrounding the implant is reduced hence preventing the prosthesis adopting a spherical unnatural shape. The following theory is advanced as the reason why a pouch in accordance with the present invention prevents such undesirable contracture although it should be understood that the invention is not restricted to such theory.

The applicant's investigations indicate that the collagen bundles forming the fibrous tissue capsules which cause tightening around breast prosthesis develop in response to stress within the tissue. In such cases the predominant forces on the tissue adjacent to the anterior side of the prosthesis are along the cephalic-caudal axis and are caused principally by the influence of gravity on the prosthesis with the patient in the standing position. There may also be oblique stresses through tissue on the posterior side of the breast prosthesis due to the influence of gravity on the prosthesis plus the additional influence of the transverse pull of the pectoral muscles. The applicant's investigations furthermore indicate that fibrous tissue is not amorphous and featureless but has a definable structure. In the case of a fibrous tissue capsule surrounding a conventional breast prosthesis the predominant feature of the structure is collagen bundles running parallel to the lines of stress. These collagen bundles tend to act as ligaments taking up slack and hence causing undesirable contracture about a mammary implant.

It has previously been thought amongst surgeons that fabrics which allow fibro-cellular ingrowth also cause increased fibrous tissue formation which would tend to cause undesirable contracture in the case of a mammary prosthesis. Contrary to this belief the applicant believes that the introduction of a fabric which gives support by being inextensible in a direction parallel to the predominant lines of stress within the tissue will tend to reduce the formation of fibrous bundles in such direction in response to such stress. Indeed if the fabric is relatively extensible in a direction transverse to the predominant lines of stress then the relative lack of support in such direction may cause the body tissue to form fibrous bundles along such transverse direction. The combined effect of such extensible and relatively inextensible features of a fabric forming a pouch in accordance with the present invention encourage the formation of body tissue more akin to the natural dermis rather than the uni-directional tendon like collagen bundles which the applicant believes are responsible for undesirable capsule contracture about the implant.

Turning now to FIG. 4 it may be seen that in addition to the cephalic-caudal axis inextensible yarn comprising the fabric there are additionally oblique yarns 10 within the fabric which may be relatively extensible. It has been found that a tulle of polyester yarn (the yarn having a diameter between 0.01 and 0.5 millimeters) is appropriate. The ideal order of magnitude for the diameter of the openings 11 in the fabric is between one and two millimeters such fabric being not unlike mosquito netting or bridal veil material although it is considered that openings in the order of 0.001 millimeters to 5 millimeters would still give advantageous results.

In the embodiment above described polyester yarn of four strands has been considered appropriate in order to achieve the desired flexibility although if infection occurs after implantation it may be more difficult to rid such multifilament (as opposed to monofilament) yarn of the infection. Nylon or polypropylene may also be useful even in monofilament form.

It is envisaged that the yarn should be non-biodegradable or at least longterm biodegradable and the term "non-biodegradable" where used herein should be contemplated to mean non-biodegradable within twelve months. At present however it is considered that ideally the material utilised should be non-biodegradable for five years or more.

FIG. 5 shows the orientation of the yarn comprising the pouch material on the posterior side and it will be noted that there are strands of yarn 12 running in an oblique direction. These are intended to be inextensible yarns aligned parallel to the stresses caused by the pectoral muscles. The strength of the pectoral muscles may vary from patient to patient and consequently a surgeon may wish to remove tissue and observe fiber orientation in order that a pouch with inextensible properties in the correct direction may be chosen. In any event a pouch should always be selected such that it is relatively inextensible parallel to the lines of stress along the tissue of a particular patient.

FIG. 5 further depicts opening 13 to facilitate the insertion of the mammary prosthesis.

It may be appreciated therefore that a pouch in accordance with the present invention, once invaded by tissue will help to impart support to the fibrous tissue along the major anterior cephalic-caudal stress lines and furthermore provides a template to encourage formation of a collagen network rather than collagen arranged in parallel bundles akin to aponeurotic ligaments which tend to shorten and take up slack.

The term "equilibrium diameter" of a mammary implant as used herein shall mean the diameter of the implant when placed in such a position as it would adopt with the patient lying on her back. In the case of a double lumen mammary prosthesis the diameter is that which the implant is intended to adopt after rupture of the outer compartment.

The claims defining the invention are as follows:

1. An implantable pouch capable of receiving a mammary prosthesis, said pouch formed from a net-like material fabricated from a bio-compatible non-biodegradable yarn having one axis which is relatively inextensible as compared to at least one other axis non-parallel thereto, said net-like material forming a closed pouch, whereby said relatively inextensible axis of the anterior layer of said pouch upon implantation is aligned with the cephalic-caudal axis.

2. A pouch in accordance with claim 1 wherein the pouch material is tulle fabricated from polyester monofilament yarn of between 0.001 and 0.5 millimeters diameter the tulle having openings between 0.001 and 5 millimeters diameter; the tulle being pre-stressed before implantation so as to produce an elongated diamond pattern between the yarns comprising the material with the long axes of the diamond being parallel to the axis in which the material is intended to be relatively inextensible.

3. A pouch in accordance with either of claim 1 wherein the material of the pouch is additionally relatively inextensible on its posterior side along an oblique axis parallel to the lines of stress traditionally present on the posterior side of a breast due to the combined influence of the pectoral muscles and gravitational stresses.

4. A pouch in accordance with claim 1 wherein the extensibility of the relatively inextensible axis of the pouch is no greater than 5 percent from its equilibrium position.

5. A pouch in accordance with claim 1 wherein the relative inextensibility along one axis of the material of the pouch arises from the inclusion of layers of yarn parallel to such axis which yarn itself is relatively inextensible.

6. A pouch in accordance with claim 1 wherein the relative inextensibility along one axis arises from the manner in which the yarn is formed into the fabric rather than inherent characteristics of the yarn itself.

7. A pouch in accordance with any one of claim 1, hereof wherein the pouch material is relatively extensible along all axes non-parallel to those specified as relatively inextensible.

8. A pouch in accordance with claim 1 hereof wherein the pouch material is relatively extensible along all axes non-parallel to those specified as relatively inextensible.

9. A pouch in accordance with claim 3 hereof wherein the pouch material is relatively extensible along all axes non-parallel to those specified as relatively inextensible.

10. The implantable pouch of claim 1, wherein said bio-compatible, non-biodegradable yarn is polymeric.

11. A pouch in accordance with claim 10 wherein the material of the pouch is additionally relatively inextensible on its posterior side along an oblique axis parallel to the lines of stress traditionally present on the posterior side of a breast due to the combined influence of the pectoral muscles and gravitational stresses.

12. A pouch in accordance with claim 11 hereof wherein the pouch material is relatively extensible along all axes non-parallel to those specified as relatively inextensible.

13. A method of implanting a pouch comprising:
  (a) taking a tissue sample from a breast which is to receive a prosthesis and observing fiber orientation within the tissue;
  (b) selecting a pouch capable of receiving a mammary prosthesis, said pouch formed from a net-like material fabricated from a bio-compatible non-biodegradable yarn having one axis which is relatively inextensible as compared to at least one other axis non-parallel thereto;
  (c) placing the prosthesis within the pouch;
  (d) inserting the prosthesis-containing pouch within the breast in such an orientation that the pouch is relatively inextensible in a direction parallel to the lines of stress in the breast as indicated by the tissue sample.

14. A method of implanting a pouch comprising:
  (a) selecting a pouch capable of receiving a mammary prosthesis, said pouch formed from a net-like material fabricated from a bio-compatible non-biodegradable yarn having one axis which is relatively inextensible as compared to at least one other axis non-parallel thereto, the pouch having a diameter up to 40 percent greater than the equilibrium diameter of the prosthesis which it is to contain;
  (b) placing the prosthesis within the pouch;
  (c) locating the prosthesis-containing pouch in the breast such that the relatively inextensible axis of the anterior layer of the pouch is aligned with the cephalic-caudal axis.

15. A method for implanting a pouch in a breast comprising:
  (a) providing a pouch capable of receiving a mammary prosthesis, said pouch being formed from a net-like material fabricated from a bio-compatible non-biodegradable yarn and having one axis which is relatively inextensible as compared to at least one other axis non-parallel thereto; and
  (b) implanting the pouch in a breast such that the relatively inextensible axis of the anterior layer of the pouch is aligned with the cephalic-caudal axis.

* * * * *